US009330803B2

(12) United States Patent
Sweat et al.

(10) Patent No.: US 9,330,803 B2
(45) Date of Patent: *May 3, 2016

(54) RADIATION THERAPY APPARATUS WITH AN APERTURE ASSEMBLY AND ASSOCIATED METHODS

(71) Applicant: .DECIMAL, INC., Sanford, FL (US)

(72) Inventors: Richard L. Sweat, Sanford, FL (US); Kevin Erhart, Orlando, FL (US); Salvadore Gerace, Orlando, FL (US)

(73) Assignee: .DECIMAL, INC., Sanford, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/585,454

(22) Filed: Dec. 30, 2014

(65) Prior Publication Data

US 2015/0119627 A1  Apr. 30, 2015

Related U.S. Application Data

(63) Continuation of application No. 13/834,772, filed on Mar. 15, 2013, now Pat. No. 8,952,345.

(51) Int. Cl.
*G21K 5/04* (2006.01)
*A61N 5/10* (2006.01)
*G21K 1/10* (2006.01)
*G21K 1/02* (2006.01)

(52) U.S. Cl.
CPC .............. *G21K 5/04* (2013.01); *A61N 5/1042* (2013.01); *A61N 5/1077* (2013.01); *G21K 1/02* (2013.01); *G21K 1/10* (2013.01); *A61N 2005/1087* (2013.01); *A61N 2005/1095* (2013.01); *Y10T 29/49* (2015.01)

(58) Field of Classification Search
CPC .............. A61N 2005/1087; A61N 2005/1095; A61N 5/1042; A61N 5/1077; G21K 1/02; G21K 1/10; G21K 5/04; Y10T 29/49
See application file for complete search history.

(56) References Cited

U.S. PATENT DOCUMENTS

| 3,114,043 | A | * | 12/1963 | Thomas | G21F 5/04 378/147 |
| 3,950,651 | A | * | 4/1976 | Flocee | A61B 6/06 378/147 |
| 6,080,992 | A | * | 6/2000 | Nonaka | G21K 1/046 250/492.3 |
| 6,980,871 | B1 | * | 12/2005 | Sweat | A61N 5/1042 378/156 |
| 8,208,601 | B2 | * | 6/2012 | Comer | A61N 5/1042 378/145 |
| 8,952,345 | B2 | * | 2/2015 | Sweat | A61N 5/1042 250/492.3 |
| 2006/0280288 | A1 | * | 12/2006 | Speiser | A61N 5/1042 378/65 |
| 2009/0096179 | A1 | * | 4/2009 | Stark | A61N 5/10 280/47.34 |

(Continued)

*Primary Examiner* — Nicole Ippolito
*Assistant Examiner* — Wyatt Stoffa
(74) *Attorney, Agent, or Firm* — Allen, Dyer, Doppelt, Milbrath & Gilchrist, P.A.

(57) ABSTRACT

A radiation therapy apparatus includes a housing, a radiation source carried by the housing, and at least one aperture assembly carried by the housing. The aperture assembly includes a radiation aperture body having a shaped opening therein to control a radiation dosing profile, and an aperture holder with an aperture-receiving passageway therein receiving the radiation aperture body, and having a recessed end. A cover is received within the recessed end of the aperture holder and retains the radiation aperture body within the aperture holder. The cover has an opening aligned with the shaped opening in the radiation aperture body. The radiation aperture body, the aperture receiving passageway of the aperture holder and the opening of the cover have angled interfaces therebetween. A radiation filter is carried by the housing.

23 Claims, 4 Drawing Sheets

(56) References Cited

U.S. PATENT DOCUMENTS

2010/0091378 A1* 4/2010 Norman .................. G21K 1/02
            359/641
2011/0127443 A1* 6/2011 Comer ................ A61N 5/1042
            250/396 R
2011/0299919 A1* 12/2011 Stark ........................ A61N 5/10
            403/321
2013/0072744 A1* 3/2013 Moskvin .............. A61N 5/1045
            600/1
2013/0221243 A1* 8/2013 Perkins ................ A61N 5/1042
            250/492.3

* cited by examiner

RADIATION THERAPY APPARATUS WITH AN APERTURE ASSEMBLY AND ASSOCIATED METHODS

RELATED APPLICATIONS

This application is a continuation of prior filed application Ser. No. 13/834,772 filed Mar. 15, 2013, which is incorporated herein by reference in its entirety.

FIELD OF THE INVENTION

The present invention relates to the field of radiation therapy, and more particularly, to an aperture assembly for a radiation therapy apparatus, and related methods.

BACKGROUND OF THE INVENTION

Proton therapy uses a beam of protons to irradiate diseased tissue, most often in the treatment of cancer. The chief advantage of proton therapy is the ability to more precisely localize the radiation dosage when compared with other types of external beam radiotherapy.

During treatment, a particle accelerator is used to target the diseased tissue with a beam of protons. Due to their relatively large mass, protons have little lateral side scatter in the tissue. The beam does not broaden much, stays focused on the shape of the diseased tissue and delivers low-dose side-effects to surrounding tissue. All protons of a given energy have a certain range, with very few protons penetrating beyond this range. The dose delivered to the tissue is maximum just over the last few millimeters of the particle's range, which is called the Bragg peak.

A radiation aperture body (i.e., aperture) and a radiation filter (i.e., a range compensator) are beam modifying devices that control the shape and penetration of protons during treatment of a patient. These devices are typically connected to an output of a radiation source of a radiation therapy apparatus. The radiation aperture body is typically brass and can be up to several inches thick, and has a shaped opening therein to control the radiation dosing profile. The radiation filter is three-dimensionally shaped to direct the protons to the desired target area on the patient to ensure that the target receives the correct radiation dose, while the healthy tissue surrounding the target receives substantially less radiation. Careful registration or indexing of the radiation filter and the radiation aperture body ensures that the patient has the proper exposure in the target area, such that the proton's energy is released within the target area.

A typical radiation therapy apparatus does not fully expose the radiation aperture body to the protons. Consequently, there is a border region around the perimeter of the radiation aperture body which is not exposed to the protons. As noted above, the radiation aperture body is typically brass and can be up to several inches thick. Brass is a fairly expensive material compared to other high density materials, and the excess brass in the border region adds to the cost of the radiation aperture body.

One approach to reduce the cost of the radiation aperture body is to replace a portion of the brass border region with a non-brass frame that carries the radiation aperture body, as disclosed in U.S. published patent application no. 2011/0127443. The frame and the radiation aperture body are dimensioned so that the radiation aperture body is still not fully exposed to the protons, but since the volume of the radiation aperture body is reduced, less brass is needed resulting in a cost savings. Nonetheless, there is still a need to further reduce the cost of a radiation aperture body.

SUMMARY OF THE INVENTION

In view of the foregoing background, it is therefore an object of the present invention to provide a radiation therapy apparatus with a low cost radiation aperture body.

This and other objects, features, and advantages in accordance with the present invention are provided by a radiation therapy apparatus comprising a housing, a radiation source carried by the housing, and at least one aperture assembly carried by the housing. The aperture assembly may comprise a radiation aperture body, an aperture holder and a cover. A radiation filter may also be carried by the housing. The radiation source may generate protons, for example.

More particularly, the radiation aperture body may have a shaped opening therein to control a radiation dosing profile. The aperture holder may have an aperture-receiving passageway therein receiving the radiation aperture body, and a recessed end. The cover may be received within the recessed end of the aperture holder, and retains the radiation aperture body within the aperture holder. The cover may have an opening aligned with the shaped opening in the radiation aperture body.

The aperture holder and cover may advantageously be formed out of a different material from the radiation aperture body. For example, the radiation aperture body may be formed out of brass, whereas the aperture holder and cover may each be formed out of stainless steel or other high density material other than brass. Since the volume of the radiation aperture body has been significantly reduced, significantly less brass may be needed resulting in an even greater cost savings.

The radiation source may include a radiation output having a first diameter, and the opening in the cover may have a second diameter less than the first diameter. This results in the radiation aperture body being fully exposed to the radiation.

To prevent unwanted radiation from passing through an interface between the radiation aperture body and the aperture holder and cover, the radiation aperture body may comprise a frusto-conical first portion, and the aperture receiving passageway may have a corresponding shape to the frusto-conical first portion. Similarly, the radiation aperture body may comprise a frusto-conical second portion, and the opening of the cover may have a corresponding shape to the frusto-conical second portion. The recessed end of the aperture holder and the cover may also define a threaded joint therebetween.

The radiation aperture body may comprise at least one alignment edge extending outwards therefrom, and the aperture-receiving passageway may further include at least one recess receiving the at least one alignment edge.

Another aspect of the present invention is directed to an aperture assembly for radiation therapy, as described above.

Yet another aspect of the present invention is directed to a method for making an aperture assembly for radiation therapy. The method may comprise forming a radiation aperture body having a shaped opening therein to control a radiation dosing profile. An aperture holder having a disk shape, an aperture-receiving passageway therein to receive the radiation aperture body, and a recessed end is formed. The method may further comprise forming a cover received within the recessed end of the aperture holder, with the cover to retain the radiation aperture body within the aperture holder, and with the cover having an opening aligned with the shaped opening in the radiation aperture body.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
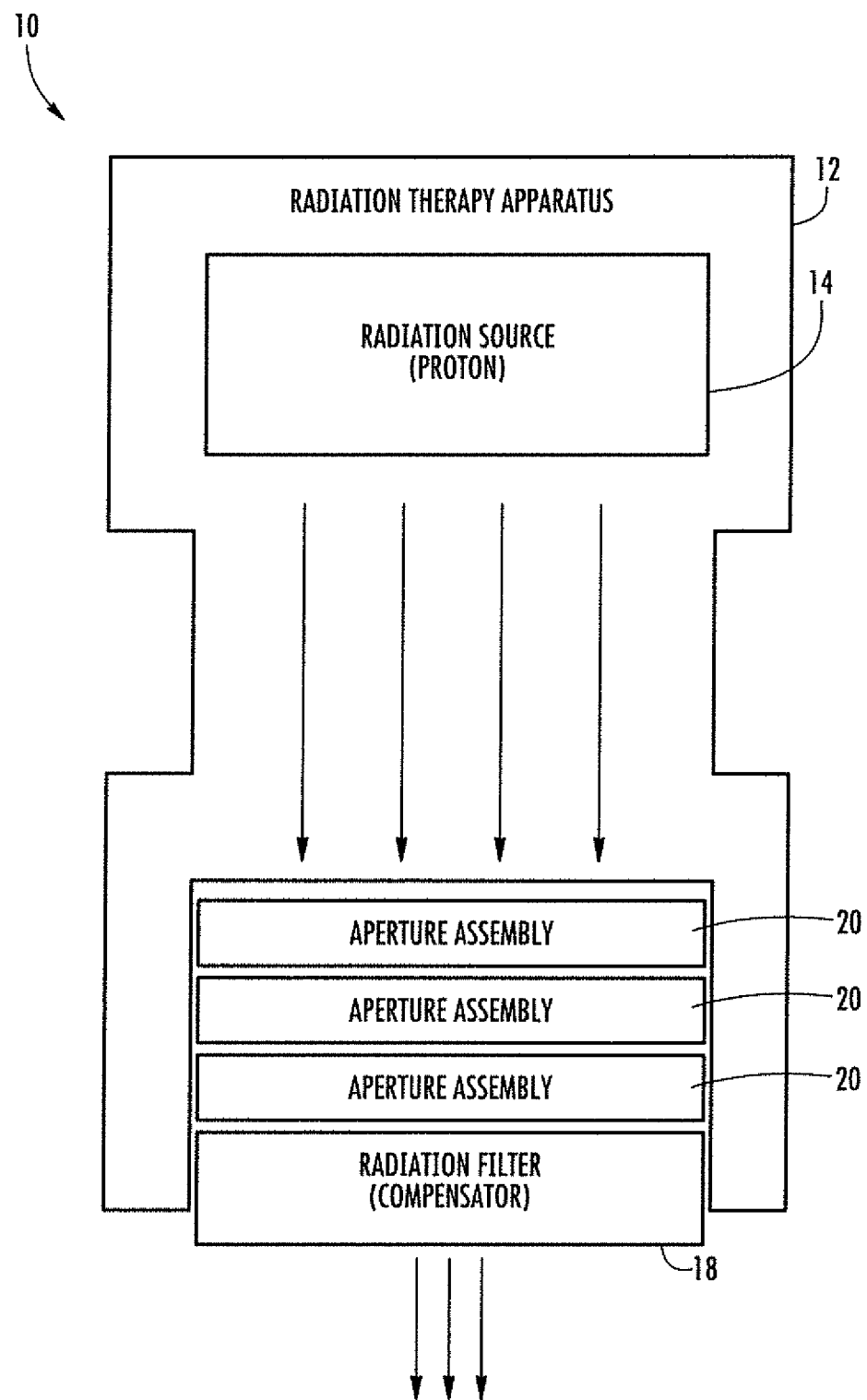
FIG. 1 is a block diagram of a radiation therapy apparatus in accordance with the present invention.

Referring initially to FIG. 1, a radiation therapy apparatus 10 includes a housing 12, a radiation source 14 carried by the housing, at least one aperture assembly 20 carried by the housing, and a radiation filter 18 carried by the housing. In the illustrated embodiment, three aperture assemblies 20 are stacked on top of one another. If the penetration energy of the radiation is low, then only one aperture assembly 20 may be sufficient to block radiation from healthy tissue within the patient. However, if the penetration energy of the radiation is high, then multiple aperture assemblies 20 may be combined to provide a total thickness necessary to block radiation from healthy tissue within the patient. Even though a single aperture assembly 20 having the same combined thickness could be used, the weight would make it difficult to handle.

The radiation filter 18 is also known as a range compensator and filters the radiation. Filter is broadly used to include controlling the intensity or range of the radiation depending on modality, as readily understood by those skilled in the art. The radiation filter 18 is specifically designed for the patient. The radiation filter 18 may be machined from a solid piece of material, and is mounted directly in the path of the radiation beam, as disclosed in U.S. Pat. No. 6,980,871. This patent is assigned to the current assignee of the present invention, and is incorporated herein by reference in its entirety. The unique three-dimensional geometry of each radiation filter 18 provides the conformal radiation dose distributions required by the patient.

The illustrated radiation source 14 is configured to generate protons. The radiation source 14 includes a particle accelerator, either a synchrotron or a cyclotron, to accelerate the protons to variable energies into a beam transport line. A synchrotron contains a ring of magnets that constrains the protons so that they travel in a set path inside a high vacuum chamber. During each revolution of travel through the chamber, the protons gain an increment of energy from the radio frequency power. After many cycles, the protons reach the energy required by the specific treatment planning system and are extracted from the ring of magnets into the beam transport line, which directs the protons to the aperture assemblies 20. Even though the illustrated radiation source 14 is a proton radiation source, the aperture assembly 20 is readily applicable to other types of radiation sources, such as electrons or photons, as readily appreciated by those skilled in the art.

The aperture assembly 20 will now be discussed in greater detail. Each aperture assembly 20 includes a radiation aperture body 30, an aperture holder 40 and a cover 50, as illustrated by the exploded view in FIG. 2 and the cross-sectional view in FIG. 3. The radiation aperture body 30 may also be referred to as an aperture. The radiation aperture body 30 has a shaped opening 32 therein specific to the patient to control a radiation dosing profile of the protons. The radiation aperture body 30 is typically made out of brass, for example. As an alternative to brass, other high density materials capable of blocking protons may be used.

The aperture holder 40 has an aperture-receiving passageway 42 therein receiving the radiation aperture body 30, and has a recessed end 44. The cover 50 is received within the recessed end 44 of the aperture holder 40 and retains the radiation aperture body 30 within the aperture holder. The illustrated aperture holder 40 has a disk shape. The shape of the aperture holder 40 is not limited to a disk shape. Instead, the shape is based upon the profile of the radiation output or snout of the radiation source 14. In other embodiments, the aperture holder 40 may have a rectangular shape, for example.

The cover 50 has an opening 52 aligned with the shaped opening 32 in the radiation aperture body 30. Aligned in this instance means that the opening 52 is not overlapping or blocking the shaped opening 32 in the radiation aperture body 30. The aperture holder 40 and cover 50 are typically made out of a non-brass material, such as stainless steel, for example. As an alternative to stainless steel, other high density materials capable of blocking protons may be used.

As a result of the aperture holder 40 and the cover 50, the volume of the radiation aperture body 30 has been significantly reduced. Since the aperture holder 40 and the cover 50 are reusable, significantly less brass is needed, a greater cost savings may be achieved. As discussed in the background section, prior art radiation aperture bodies were not fully exposed to the protons. In other words, the outside diameter of the radiation aperture body exceeded the diameter of the radiation output. This ensured that there were no interfaces being exposed to the protons that would allow the protons to penetrate through and onto the patient receiving treatment.

Figure 3:
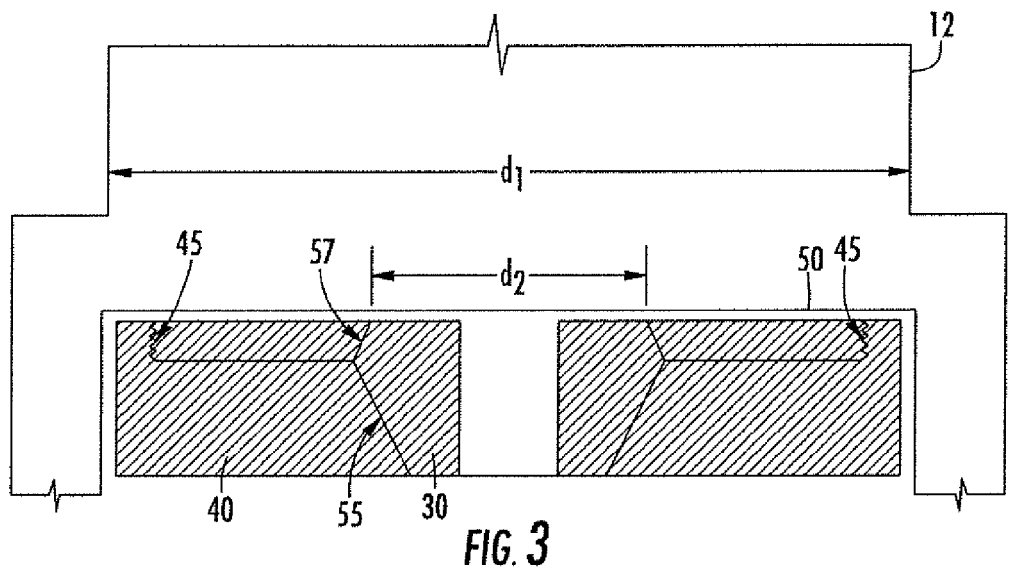
FIG. 3 is a cross-sectional side view of the aperture assembly illustrated in FIG. 1.

In sharp contrast, the radiation aperture body 30 is fully exposed to the protons. In other words, the radiation source 14 includes a radiation output having a first diameter $d_1$, and the opening 52 in the cover 50 has a second diameter $d_2$ less than the first diameter, as illustrated in FIG. 3. This notably causes the interface 57 between the radiation aperture body 30 and cover 50, as well as the interface 55 between the radiation aperture body 30 and the aperture holder 40, to be fully exposed.

To prevent unwanted radiation from passing through the interfaces 57, 55 between the radiation aperture body 30 and the aperture holder 40 and cover 50, the radiation aperture body has a frusto-conical first portion 36, and the aperture receiving passageway 42 has a corresponding shape to the frusto-conical first portion. Similarly, the radiation aperture body 30 has a frusto-conical second portion 38, and the opening 52 of the cover 50 may have a corresponding shape to the frusto-conical second portion.

As a result of the frusto-conical portions 36, 38 of the radiation aperture body 30, the interfaces 57, 55 are angled. This advantageously reduces any chance of unwanted protons making their way to the patient, as compared to vertical interfaces, by increasing the relative angle between the radiation particles and the interfaces 57, 55. The frusto-conical portion 36 also allows the radiation aperture body 30 to be press fit into the aperture holder 40, ensuring unwanted radiation does not pass through the interface 55. Similarly, the frusto-conical portion 38 also allows the cover 50 to be press fit onto the radiation aperture body 30, ensuring unwanted radiation does not pass through the interface 57.

In other embodiments, the radiation aperture body 30 may include only one frusto-conical portion 36 or 38. The other non-frusto-conical portion may be configured so that one of the interfaces 57 or 55 is at a vertical angle with respect to an upper surface of the aperture holder 40.

Another area of concern for radiation leakage is at the interface 45 between the aperture holder 40 and the cover 50. To address this concern, the recessed end 44 of the aperture holder 40 and the cover 50 define a threaded joint therebetween. In other words, the recessed end 44 and the cover 50 are threaded for engaging one another to define the threaded joint. The interface 45 may also be angled.

Figure 2:
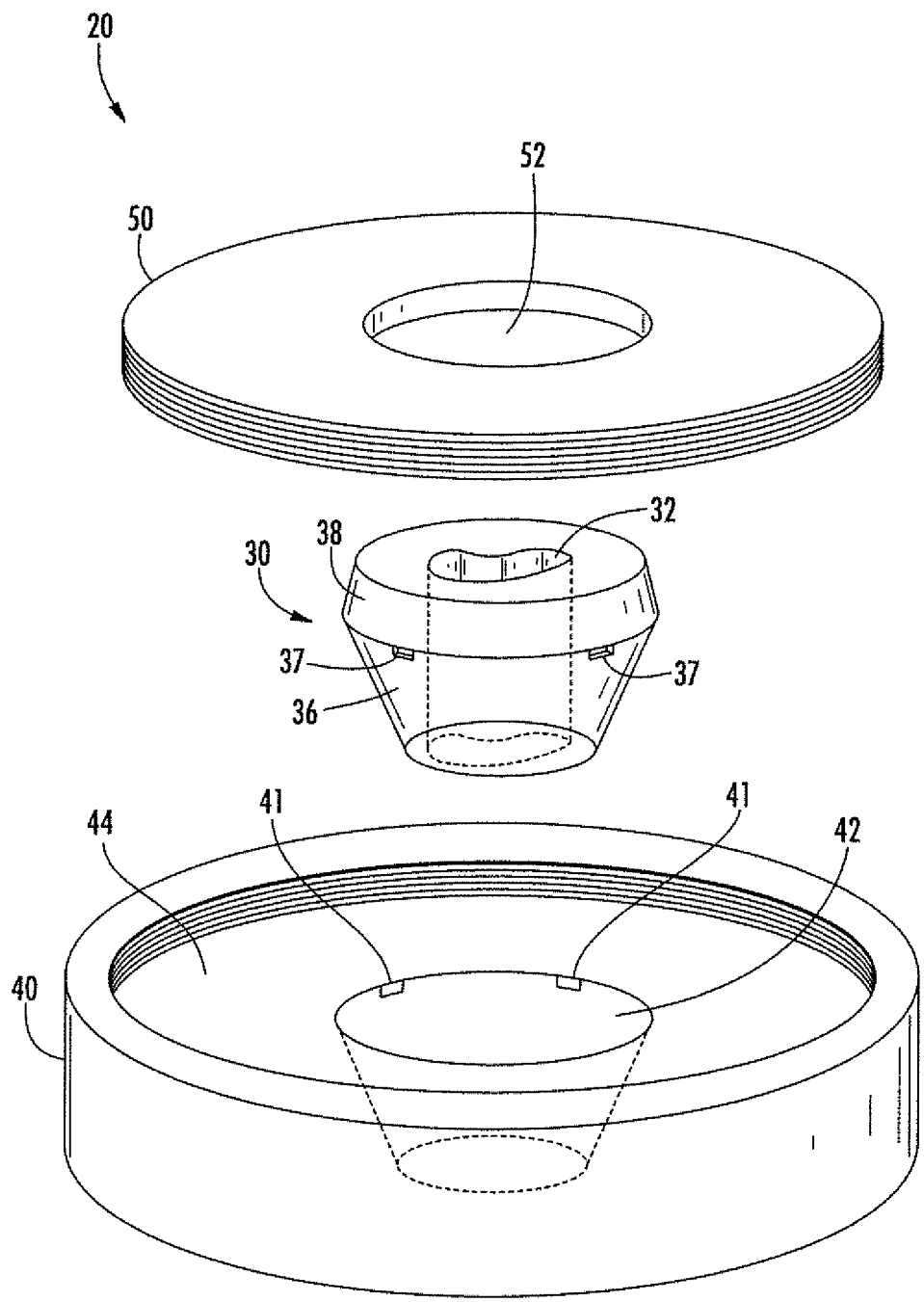
FIG. 2 is an exploded perspective view of the aperture assembly illustrated in FIG. 1.
Figure 4:
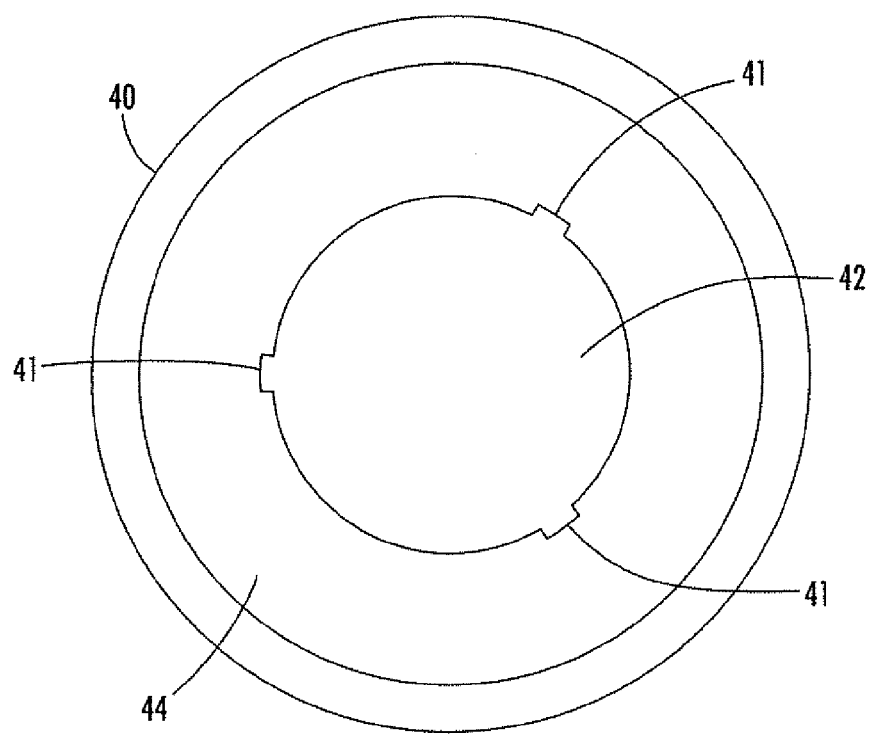
FIG. 4 is a top view of the aperture holder illustrated in FIG. 2 without the radiation aperture body within the aperture-receiving passageway.

To place the radiation aperture body 30 in a desired orientation, the radiation aperture body includes at least one alignment edge 37 extending outwards therefrom, as illustrated in FIG. 2. The aperture-receiving passageway 42 include at least one recess 41 receiving the at least one alignment edge, as illustrated in FIG. 4. In the illustrated embodiment, there are three alignment edges 37 and three corresponding recesses 41. The alignment edges 37 and recesses 41 prevent spinning of the radiation aperture body 30 once placed in the aperture-receiving passageway 42.

Figure 5:
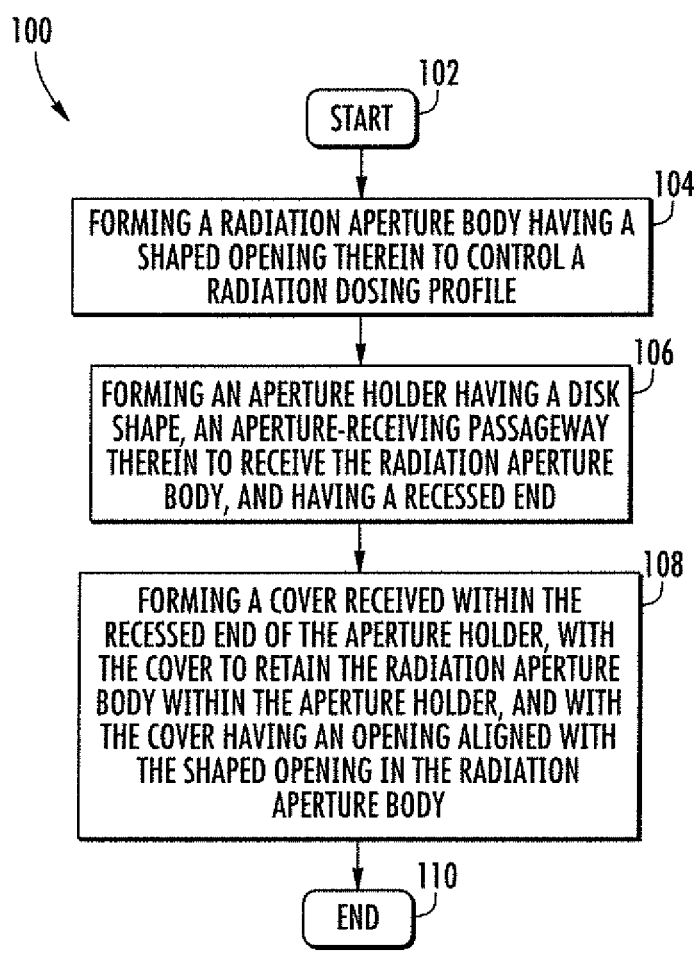
FIG. 5 is a flowchart illustrating a method for making the aperture assembly for radiation therapy illustrated in FIG. 1.

Referring now to the flowchart 100 in FIG. 5, another aspect is directed to a method for making an aperture assembly 20 for radiation therapy. The method comprises, from the start (Block 102), forming a radiation aperture body 30 at Block 104 having a shaped opening 32 therein to control a radiation dosing profile. An aperture holder 40 is formed at Block 106 having a disk shape, an aperture-receiving passageway 42 therein to receive the radiation aperture body 30, and having a recessed end 44. The method further comprises forming a cover 50 at Block 108 that is received within the recessed end 44 of the aperture holder 40. The cover 50 retains the radiation aperture body 30 within the aperture holder 40. The cover 50 has an opening 52 aligned with the shaped opening 32 in the radiation aperture body 30. The method ends at Block 110.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A radiation therapy apparatus comprising:
   a housing;
   a radiation source carried by said housing;
   at least one aperture assembly carried by said housing and comprising
      a radiation aperture body having a shaped opening therein to control a radiation dosing profile of a radiation beam,
      an aperture holder, an aperture-receiving passageway therein receiving said radiation aperture body, and having a recessed end, and
      a cover received within the recessed end of said aperture holder and retaining said radiation aperture body within said aperture holder, said cover having an opening aligned with the shaped opening in said radiation aperture body, and
      said radiation aperture body, the aperture receiving passageway of said aperture holder and the opening of said cover having inclined interfaces therebetween with respect to a path of the radiation beam;
   a radiation filter carried by said housing.

2. The radiation therapy apparatus according to claim 1 wherein said at least one aperture assembly comprises a plurality of stacked aperture assemblies.

3. The radiation therapy apparatus according to claim 1 wherein said radiation aperture body comprises a frusto-conical first portion; and wherein the aperture receiving passageway has a corresponding shape to the frusto-conical first portion.

4. The radiation therapy apparatus according to claim 1 wherein said radiation aperture body comprises a frusto-conical second portion; and wherein the opening of said cover has a corresponding shape to the frusto-conical second portion.

5. The radiation therapy apparatus according to claim 1 wherein the recessed end of said aperture holder and said cover define a threaded joint therebetween.

6. The radiation therapy apparatus according to claim 1 wherein said radiation aperture body comprises at least one alignment edge extending outwards therefrom; and wherein the aperture-receiving passageway further includes at least one recess receiving the at least one alignment edge.

7. The radiation therapy apparatus according to claim 1 wherein said radiation aperture body comprises brass.

8. The radiation therapy apparatus according to claim 1 wherein said aperture holder and said cover each comprises stainless steel.

9. The radiation therapy apparatus according to claim 1 wherein said radiation source generates protons.

10. An aperture assembly for radiation therapy comprising:
    a radiation aperture body having a shaped opening therein to control a radiation dosing profile of a radiation beam;
    an aperture holder, an aperture-receiving passageway therein receiving said radiation aperture body, and having a recessed end; and
    a cover received within the recessed end of said aperture holder and retaining said radiation aperture body within said aperture holder, said cover having an opening aligned with the shaped opening in said radiation aperture body;
    said radiation aperture body, the aperture receiving passageway of said aperture holder and the opening of said cover having inclined interfaces therebetween with respect to a path of the radiation beam.

11. The aperture assembly according to claim 10 wherein said aperture holder has a disk shape.

12. The aperture assembly according to claim 10 wherein said aperture holder has a rectangular shape.

13. The aperture assembly according to claim 10 wherein the recessed end of said aperture holder and said cover define a threaded joint therebetween.

14. The aperture assembly according to claim 10 wherein said radiation aperture body comprises at least one alignment edge extending outwards therefrom; and wherein the aperture-receiving passageway further includes at least one recess receiving the at least one alignment edge.

15. The aperture assembly according to claim 10 wherein said radiation aperture body comprises brass.

16. The aperture assembly according to claim 10 wherein said aperture holder and said cover each comprises stainless steel.

17. A method for operating a radiation therapy apparatus comprising:
   providing a radiation source to generate a radiation beam;
   positioning at least one aperture assembly within the radiation beam, the at least one aperture assembly comprising
      a radiation aperture body having an exposed upper surface with a shaped opening therein to control a radiation dosing profile,
      an aperture holder, an aperture-receiving passageway therein receiving the radiation aperture body, and having a recessed end, and
      a cover received within the recessed end of the aperture holder and retaining the radiation aperture body within the aperture holder, the cover having an opening aligned with the exposed upper surface of the radiation aperture body so as to define an interface therebetween that is exposed to the radiation beam,
      the radiation aperture body, the aperture receiving passageway of the aperture holder and the opening of the cover having inclined interfaces therebetween with respect to a path of the radiation beam; and
   positioning a radiation filter adjacent the at least one aperture assembly.

18. The method according to claim 17 wherein the radiation aperture body comprises a frusto-conical first portion; and wherein the aperture receiving passageway has a corresponding shape to the frusto-conical first portion.

19. The method according to claim 17 wherein the radiation aperture body comprises a frusto-conical second portion; and wherein the opening of the cover has a corresponding shape to the frusto-conical second portion.

20. The method according to claim 17 wherein the recessed end of the aperture holder and the cover define a threaded joint therebetween.

21. The method according to claim 17 wherein the radiation aperture body comprises at least one alignment edge extending outwards therefrom; and wherein the aperture-receiving passageway further includes at least one recess receiving the at least one alignment edge.

22. The method according to claim 17 wherein the radiation aperture body comprises brass.

23. The method according to claim 17 wherein the aperture holder and the cover each comprises stainless steel.

* * * * *